United States Patent [19]

Kneen

[11] Patent Number: 4,535,183

[45] Date of Patent: Aug. 13, 1985

[54] PHARMACEUTICAL COMPOUNDS, PREPARATION, USE AND INTERMEDIATES THEREFOR AND THEIR PREPARATION

[75] Inventor: Geoffrey Kneen, Bromley, England

[73] Assignee: Burroughs Wellcome Co., Research Triangle Park, N.C.

[21] Appl. No.: 332,246

[22] Filed: Dec. 18, 1981

[30] Foreign Application Priority Data

Dec. 18, 1980 [GB] United Kingdom ............... 8040512

[51] Int. Cl.$^3$ ............................................. C07C 65/40
[52] U.S. Cl. ....................................... 514/568; 560/53; 562/463; 514/815; 514/520; 514/381; 514/605
[58] Field of Search ........................ 562/463; 560/53; 424/308, 317

[56] References Cited

U.S. PATENT DOCUMENTS 3,914,286 10/1975 Mieville ............................... 560/52

OTHER PUBLICATIONS

Dean, J. et al., New England Journal of Med., vol. 299, No. 14, pp. 752–763, 804–811, 863–870, (1978).

*Primary Examiner*—Paul J. Killos
*Attorney, Agent, or Firm*—Donald Brown

[57] ABSTRACT

This invention is directed to novel ether compounds of formula (I)

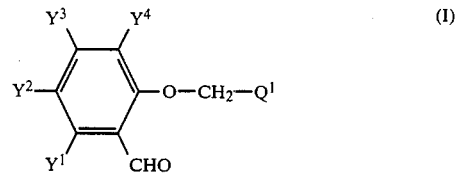

which are of value in medicine in the palliation of haemoglobinopathies, in particular sickle-cell anemia, and also in the palliation of pulmonary dyefunction, protection from the effects of hypoxia and the radio-sensitization of tumours. The invention is also directed to methods for the preparation of the ether compounds, to pharmaceutical formulations containing them, the preparation of such formulations and the use of the compounds in human medicine. Also provided by the invention are intermediates of value in the preparation of the ether compounds, by the methods described, and the preparation of the intermediates.

21 Claims, 1 Drawing Figure

FIG.1

PHARMACEUTICAL COMPOUNDS, PREPARATION, USE AND INTERMEDIATES THEREFOR AND THEIR PREPARATION

This invention relates to ethers useful in medicine, to the preparation of such compounds, to pharmaceutical formulations containing such compounds and the preparation of such formulations, to the use of the compounds in medicine, and to novel intermediates for the said compounds and the preparation thereof.

The present invention more particularly relates to the novel ether compounds of formula (I), as hereinafter defined, which are of value in medicine in the palliation of haemoglobinopathies including and in particular sickle-cell anaemia.

Sickle-cell anaemia is essentially a disease of childhood. The major manifestatations are a chronic haemolytic anaemia and vaso-occlusive crises that cause severe pain as well as long-term and widespread organ damage. In addition there are systemic effects such as increased susceptibility to infections and impaired growth and development.

The behaviour of the haemoglobin (predominantly "sickle haemoglobin", referred to as Hb-S) in erythrocytes (red blood cells) from sickle-cell anaemia sufferers differs from that of the haemoglobin in erythocytes from normal adults (predominantly the Rb-A form) in the following important aspects.

(A) The oxygen-dissociation curve. When a graph is plotted of the percentage saturation of haemoglobin with oxygen (ordlnate) against the partial pressure of oxygen, sometimes called the oxygen tension (abscissa) a characteristic sigmold curve is obtained. With respect to the curve obtained with whole blood from normal adults, that obtained with whole blood from sickle-cell anaemia sufferers is disabled to the right. That is to say, the haemoglobin in the sickle-cell erythrocytes has a reduced oxygen affinity compared with that in the normal erythrocytes, a higher oxygen tension being required to produce a given percentage saturation.

(B) The deoxyhaemoglobin tetramer. When erythrocytes from sickle-cell anaemia sufferers are deoxygenated in vitro under physiological conditions the Hb-S therein aggregates into long 'polymers', non-covalently linked arrays of deoxy Hb-S molecules which align themselves into viscous paracrystalline gels. This deoxygenation-dependent gelation is accompanied by deformation of the erythrocyte (commonly termed sickling) into characteristic sickle and holly-leaf forms and by a lost of deformability. No such behaviour is observed with erythrocytes from normal adult individuals. The gelation and sickling can be reversed by oxygenation, i.e. conversion of the deoxy Hb-S to the oxygenated conformation, except for a proportion identified as irreversibly sickled cells (ISC's) which are characterised by their inability to resume the normal biconcave disc shape even after dissolution of the Hb-S gel.

Although the exact relationships are as yet incompletely understood the gelation, sickling and loss of deformability are known to be involved in the pathophysiology of the disease: typically between 30 and 60 percent of the erythrocytes in venous blood from sickle-cell anaemia sufferers are sickled.

Because it has its orgins in a genetic defect no true cure for sickle-cell anaemia is possible short of genetic manipulation. At present, effective medical intervention is restricted to supportive care, treatment of infections and therapies directed towards particular organ involvement. The prime objective of much current research is a drug that will compensate for the fundamental defect of sickle-cell anaemia but as yet no compound has proved to be both sufficiently efficacious and safe to be generally acceptable (for a review see "Sickle-cell anaemia: Molecular and cellular bases of therapeutic approaches" by J. Dean and A. N. Schechter. *New England Journal of Medicine,* 299 (1978) pp 752–763, 804–811 and 863–870).

The compounds of formula (I), as hereinafter defined, are effective in the palliation of sickle-cell anaemia (i.e. in alleviating the symptoms of the disease and in mitigating the sufferings of those having the condition) and in particular exhibit the following properties:

(A) They induce a left-displacement of the oxygen-dissociation curve of whole normal (AA genotype) human blood in vitro, i.e. the oxygen affinity is increased and the oxygenated conformation of the Hb-A is stabilized.

(B) They induce a left-displacement in vivo of the oxygen-dissociation curve of whole rat blood.

(C) They prevent the onset of sickling in vitro in whole homozygous (SS genotype) human sickle-cell blood.

In formula (I), as set forth above, $Y^1$ is selected from hydroxyl, alkylamino of 1 to 4 carbon atoms and alkanoylamino having 1 to 4 carbon atoms in the alkyl moiety thereof;

$Y^2$, $Y^3$ and $Y^4$ are independently selected from hydrogen, halogen, alkyl of 1 to 4 carbon atoms, alkoxy of 1 to 4 carbon atoms, trifluoromethyl, hydroxyl and benzyloxy; and $Q^1$ in either where

$Q^2$ and $Q^3$ are independently selected from hydrogen and alkyl of 1 to 4 carbon atoms;

X is selected from cyano, carboxyl or a derivative thereof, 5-tetrazolyl and alkylsulphonylcarbamoyl having 1 to 6 carbon atoms in the alkyl moiety thereof; and n is 0 or an integer selected from 1, 2, 3, 4, 5 and 6; together with salts thereof, provided that when $Y^1$ is hydroxyl, $Y^2$, $Y^3$ and $Y^4$ are all hydrogen and $Q^1$ is either then X is alkylsulphonylcarbamoyl.

The halogen identities for $Y^2$, $Y^3$ and $Y^4$ may be selected from iodine, bromine, chlorine and fluorine.

The alkyl identities for $Q^2$ and $Q^3$ preferably have 1 to 2 carbon atoms (i.e. methyl or ethyl) and are desirably methyl.

Compounds within formula (I) wherein X is carboxyl derivative include:

esters, including aliphatic and aromatic hydrocarbon esters such as alkyl and aralkyl esters where for example the alkyl has 1 to 12 and preferably 1 to 4 carbon atoms (in particular methyl, ethyl, isopropyl and t-butyl) and where the aralkyl is for example benzyl; and amides, including the unsubstituted amide, N-substituted amides and N,N-disubstituted amides (embracing cyclic and heterocyclic amides) where the substiuent group(s) is (are) for example aliphatic hydrocarbon such as alkyl, in particular alkyl of 1 to 4 carbon atoms such as methyl, ethyl, isopropyl and t-butyl.

In the salts of the compounds of formula (I) the biological activity resides in ether (anion) moiety and the identity of the cation is of less importance although for use in medicine it is preferably pharmacologically acceptable to the recipitent. Suitable salts include ammonium salts, alkali metal salts such as sodium and potassium salts, and salts formed with organic bases.

Compounds of formula (I) wherein $Y^1$ is alkylamino can form acid addition salts; in such salts the biological activity resides in the ether moiety and the identity of the acid is of less importance although for use in medicine it is preferably pharmacologically acceptable to the recipient. Suitable acids are well known in the art, for example hydrochloric acid and acetic acid.

As a subclass within formula (I) may be mentioned the compounds wherein

X is selected from cyano, 5-tetrazolyl, alkylsulphonylcarbamoyl having 1 to 6 carbon atoms in the alkyl moiety thereof and a group —CO, Y, where Y is —OR$^1$ and R$^1$ is hydrogen, alkyl of 1 to 4 carbon atoms or benzyl, or Y is —NR$^2$R$^3$ where R$^2$ and R$^3$ are independently hydrogen or alkyl of 1 to 4 carbon atoms, together with salts thereof.

Preferred within formula (I) are those compounds wherein X is carboxyl, together with salts thereof.

A particular preferred compound is chemically named 4-(2-formyl-3-hydroxyphenoxymethyl)benzoic acid, together with salts thereof.

Where the compounds of formula (I), as above defined, include an asymmetric centre the said formula should be understood to include all optical isomers embraced thereby and mixtures thereof.

The compounds of formula (I) and their salts may be prepared by those methods known in the art for the synthesis of compounds of analogous structure and in this regard reference is made, by way of illustration only, to the following standard texts:

(i) *"Protective Groups in Organic Chemistry"*, ed. J. F. W. McOmie, Plenum Press (1973), ISBN 0-306-30717-0;

(ii) *"Compendium of Organic Synthetic Methods"*, ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4; and (iii) Rodd's *"Chemistry of Carbon Compounds"*, second edition, Elsevier Publishing Company.

All references identified hereinabove or in the following are hereby incorporated herein by reference thereto.

(1) One method comprises reaction of the phenol (II) with alkane derivative (III)

wherein $Y^1$, $Y^2$, $Y^3$, $Y^4$ and $Q^1$ are as defined in formula (I) and $Z^1$ is a leaving atom or group.

As one possibility $Z^1$ is selected from for example halo (such as bromo, when a catalytic amount of for example sodium iodide is desirably present), arylsulphonyloxy such as p-toluenesulphonyloxy and alkylsulphonyloxy such as methanesulphonyloxy, the reaction being carried out under basic conditions.

The reaction may thus for example be effected in the presence of an alkali metal carbonate such as potassium carbonate, an alkali metal alkoxide such as sodium or potassium ethoxide or an alkali metal hydride such as sodium hydride and in a solvent such as a lower alkanol (for example, ethanol) or an aliphatic ketone (for example, acetone or methylethylketone), and is conducted at elevated temperatures, preferably at the reflux temperature of the reaction mixture. As an alternative, the alkali metal hydride may be employed at ambient temperature in a solvent such as dioxan, tetrahydrofuran, dimethylsulphoxide, acetonitrile, dimethylformamide or dimethylacetamide.

In an alternative procedure (II) is reacted in the presence of triphenylphosphine and diethyl azodicarboxylate with a compound (III) having $Z^1$ as hydroxyl, the reaction being conducted under an inert atmosphere (for example nitrogen or argon) and in a polar aprotic medium.

(2) For compounds wherein $Y^1$ is hydroxyl, a further method comprises conversion of an ether (IV)

wherein $Y^2$, $Y^3$, $Y^4$ and $Q^1$ are as defined in formula (I), $-OZ^2$ is hydroxyl or a group convertible thereto and $Z^3$ is formyl or a group convertible thereto and where $Z^3$ is other than formyl when $-OZ^2$ is hydroxyl, or $-OZ^2$ and $Z^3$ together comprise a ring system that can be selectively cleaved to provide the o-hydroxy-formyl function.

Suitable identities for the moiety $Z^2$ include alkyl, for example alkyl of 1 to 4 carbon atoms and in particular methyl, ethyl, isopropyl and t-butyl; aralkyl such as benzyl; acyl such as alkanoyl, in particular alkanoyl where the alkyl moiety therein has 1 to 4 carbon atoms, for example acetyl; methoxymethyl; methoxyethoxymethyl; and tetrahydropyranyl. Such groups may be removed, i.e. replaced by hydrogen, by methods standard in the art. Thus removal of an alkyl group may be effected using for example magnesium iodide or sodium thiocresolate or (at reduced temperatures) by use of an agent such as boron trichloride or tribromide in a medium such as dichloromethane; an acyl group may be removed by base hydrolysis; an alkyl group, methoxymethyl, methoxyethoxymethyl and tetrahydropyranyl may be removed by acid hydrolysis; and hydrogenolysis (for example using a palladium charcoal catalyst) may be used to remove an aralkyl group.

Suitable identities for $Z^3$ include conventional protecting groups for aldehydes such as acetal, thioacetal (mercaptal), oxime, hydrazone (including phenylhydrazone), semicarbazone and anil (Schiff base) functions. The formyl group can be generated therefrom by standard procedures, for example by acid or base hydrolysis or, in the case of thioacetals, by treatment with mercuric chloride in the presence of cadmium carbonate.

As further possible identities for $Z^3$ may be mentioned groups selectively oxidisable to the formyl group. Thus when $Z^3$ is methyl the compound of formula (I) may be obtained by use of chromium trioxide in acetic anhydride with subsequent hydrolysis (for example dilute sulphuric or hydrochloric acid) of the initially formed benzylidene acetate; when $Z^3$ is $-CH_2OH$ suitable reagents include chromium trioxide in pyridine, pyridinium dichromate, pyridinium chlorochromate and manganese dioxide. Other suitable procedures include treatment of the corresponding benzylidene chloride ($Z^3$ is $-CHCl_2$) either with water at elevated temperatures and in the presence of iron powder as catalyst or with boric acid. The compounds of formula (I) may also be derived from the corresponding benzyl chloride ($Z^3$ is $-CH_2Cl$) by refluxing with aqueous copper or lead nitrate in a current of carbon dioxide or alternatively by refluxing with hexamethylenetetramine in aqueous ethanolic solution (Sommelet's reaction).

Further suitable techniques comprise selective reduction to the formyl group of appropriate identities for $Z^3$. In particular may be mentioned reduction of the benzoyl chloride ($Z^3$ is $-COCl$) using hydrogen and a palladium catalyst in the presence of a quinoline-sulphur poison (Rosenmund's reduction); reduction of the nitrile ($Z^3$ is $-CN$) using Raney nickel in formic acid, stannous chloride and hydrochloric acid (Stephen's method) or a reagent such as sodium triethoxyaluminium hydride, prepared from aluminium ethoxide and sodium hydride in ether or tetrahydrofuran; and reduction of an alkyl (for example methyl or ethyl) ester ($Z^3$ is $-COOM/Et$) by use of sodium diisobutylaluminum hydride (from sodium hydride and diisobutylaluminium hydride) in ether at $-70°$ C.

As another possibility, an ether (IV) wherein $Z^3$ is the 4-oxazolinyl group may be converted into a compound of formula (I) by treatment with an alkyl iodide, for example methyl iodide, to yield the quaternary N-alkyl compound followed by reduction with an agent such as sodium borohydride.

Suitable compounds within formula (IV) wherein $-OZ^3$ and $Z^3$ together comprise a ring system as above defined include the benzoforine (V) and the 1,3-benzodioxane (VI)

wherein (in (V))$Y^5$ is selected from hydrogen, alkyl (1 to 4 carbon atoms), aryl (for example phenyl), aralkyl (for example benzyl), alkanoyl having 1 to 4 carbon atoms in the alkyl moiety thereof, aranoyl (for example benzoyl) and alkanoxycarbonyl having 1 to 4 carbon atoms in the alkyl moiety thereof and (in (VI))$Z^4$ is lower alkyl such as methyl or ethyl. Conversion of the benzofurans to the compounds of formula (I) may be affected by oxomolysis and subsequent treatment with dimethylsulphide or with zinc dust in acetic acid, or by chronic acid hydrolysis. Where oxonolysis is effected of a benzofuran having $Y^5$ as alkyl, aryl or aralkyl, saponification of the (open-ring) product thereof will be required to remove said group, conveniently by use of aqueous sodium or potassium hydroxide. Conversion of the 1,3-benzodioxane to the compounds of formula (I) may be effected by acid hydrolysis.

(3) For compounds of formula (I) and salts thereof wherein $Q^1$ is a group a further method comprises selective reduction of an ether (VII)

wherein $Y^1$, $Y^2$, $Y^3$, $Y^4$ and X are as defined in formula (I) and $-Z^5-$ is a group selectively reducable to As one possibility $-Z^5-$ may be an unsaturated hydrocarbon chain which includes a vinylene or ethynylene group, as in respectively for example

Such groups may be reduced by methods standard in the art, for example a vinylene group by use of hydrogen and a catalyst such as palladium, Raney nickel or Adams' catalyst, while Adams' catalyst may also be used in respect of an ethynylene group.

As another possibility $-Z^5-$ may include an oxo group, as in for example which may be reduced to a methylene group by standard procedures such as the Clemmensen reduction using amalgamated zinc and concentrated hydrochloric acid or by heating with concentrated hydriodic acid and red phosphorus. It will be appreicated that in such circumstances the formyl group in the starting material (IV) may require initial protection and subsequent deprotection for example in the manner indicated (2) supra.

(4) The compounds of formula (I) and salts thereof may also be prepared by introduction of a formyl group into an ether (VIII)

wherein $Y^1$, $Y^2$, $Y^3$, $Y^4$ and $Q^1$ are as defined in formula (I).

As one possibility this may be effected by lithium exchange with an agent such as phenyllithium and subsequent formylation with for example dimethylformamide, N-methylformanilide or diethylphenyl orthoformate.

As an alternative procedure, those compounds of formula (I) wherein (in the group $Q^1$) X is a group stable under basic conditions (for example, carboxyl and 5-tetrazolyl) may be prepared by the Reimer-Tiemann synthesis, i.e. reaction with chloroform and a base such as pyridine or an alkali metal hydroxide or carbonate.

(5) A further method comprises conversion of a compound of formula (IX)

wherein $Y^1$, $Y^2$, $Y^3$ and $Y^4$ are as defined in formula (I), $Z^6$ is a group convertible to a group X as defined in formula (I) and $-Q^4-$ is selected, as appropriate from Thus the compounds of formula (I) having X as the 5-tetrazolyl group may be prepared by reacting a compound of formula (IX) wherein $Z^6$ is a tetrazolyl group precursor with hydrazoic acid or a salt thereof or with nitrous acid, as appropriate.

Compounds of formula (IX) wherein $Z^6$ is formyl, $-CH_2OH$ or (lower alkyl) alkanoyl such as acetyl may be converted to the carboxyl compounds of formula (I) (X is carboxyl) by standard oxidative procedures using for example acid dichromate: it will be appreciated that in such circumstances the formyl group present in (IX) and retained in the compound of formula (I) may require initial protection and subsequent deprotection, for example in the manner indicated in (2) supra. The acetyl compounds of formula (IX) may also be converted to the carboxyl compounds of formula (I) by means of the haloform reaction. The said carboxyl compounds may also be prepared by hydrolysis of the corresponding acid chlorides and (lower alkyl) mixed anhydrides such as the ethyl compounds ($Z^6$ is $-CO.O.CO.Et$).

The (lower alkyl) mixed anhydrides of formula (IX) and the acid chlorides may be converted to the esters within formula (I) by reaction with the appropriate alcohol while the amides within formula (I) may be prepared by ammonolysis of the said starting materials using ammonia or a primary or secondary amine, as appropriate.

It will be appreciated that this synthetic approach also embraces the conversion, by standard procedures, of certain of the end-product compounds of formula (I) to other compounds also within the said formula. Thus the esters may be converted to the corresponding carboxyl compounds (carboxylic acids) by hydrolysis, the corresponding salts being obtained when the hydrolysis is carried out with alkali (saponification), and to the amides by ammonolysis using, as appropriate, ammonia or a primary or secondary amine. The amides may also be prepared by treatment of the carboxyl compounds with for example triethylamine and ethyl chloroformats followed by, as appropriate, an ammonium salt or a primary or secondary amine. The unsubstituted amides may also be prepared by treating an ester with sodamide in liquid ammonia, by the action of heat upon the ammonium salts of the carboxylic acids, or by reacting the said acids with urea. The acids and, as appropriate, salts thereof may be prepared by acid or base, preferably base, hydrolysis of an amide or by the action of nitrous acid upon the unsubstituted amides. The esters may be obtained from the acids by esterification using the appropriate alcohol or, for alkyl esters having at least two carbon atoms, by treatment with the appropriate olefin in the presence of boron trifluoride. The alkyl esters may also be prepared by refluxing the silver salts of the acids in ethanol with the appropriate alkyl halide, while the methyl esters may specifically be prepared by treating the acids with diazomethane in ether. Conversion of the benzyl esters to the acids may be effected by hydrogenolysis using for example a palladium charcoal catalyst and conversion of one ester to another is possible using routine transesterification techniques.

The nitriles of formula (I) (X is cyano) may be converted by conventional hydrolysis procedures to the carboxylic acids (X is carboxyl) or, by graded hydrolysis, to the corresponding unsubstituted amides. The said nitriles may also be converted to the corresponding 5-tetrazolyl compounds of formula (I) by reaction with hydrazoic acid or a salt thereof (vid. sup.), the reaction preferably being carried out at elevated temperature with a hydrazoic acid salt such as the ammonium salt and in a polar aprotic medium such as dimethylsulphoxide or dimethylformamide.

Compounds of formula (I) wherein X is alkylsulphonylcarbamoyl may be prepared by reacting a (lower alkyl) mixed anhydride of formula (IX) (for example the ethyl or isobutyl compound) with an alkali metal salt of the appropriate alkanesulphonamide, the latter reagent being conveniently prepared in situ by for example reacting the alkanesulphonamide with sodium methoxide in method. The mixed anhydride starting material may be prepared by methods analogous to those well known in the art, for example from the corresponding carboxylic acid and a (lower alkyl) chloroformate in the presence of triethyiamine or N-methylmorpholine and in a solvent such as tetrahydromian.

(6) For compounds wherein at least one of $Y^2$, $Y^3$ and $Y^4$ is hydrogen, a further method comprises decarboxylation of a benzoic acid (X)

(X)

wherein $Y^1$ and $Q^1$ are as defined in formula (I) and one of $Z^7$, $Z^8$ and $Z^9$ is carboxyl and the other two have the same meanings as respectively $Y^2$, $Y^3$ and $Y^4$ also as defined in formula (I).

The decarboxylation may be effected by any of the conventional techniques, for example by heating (X) in quinoline in the presence of copper or with dioxane and acidic alumina.

(7) For compounds wherein $Y^1$ is alkylamino or alkanoylamino, a further method comprises conversion of an ether (XI)

(XI)

wherein $Y^2$, $Y^3$, $Y^4$ and $Q^1$ are as defined in formula (I), —$NHZ^{10}$ is alkylamino or alkanoylamino as defined in formula (I) and $Z^3$ is a group convertible to formyl or (for compounds wherein $Y^1$ is alkanoylamino) —$NHZ^{10}$ and $Z^3$ together comprise a ring system that can be selectively cleaved to provide an o-alkanoylamino formyl function.

Suitable identities for $Z^3$ together with appropriate procedures for generating the formyl group therefrom are as recited supra.

Suitable compounds within formula (XI) wherein —$NHZ^{10}$ and $Z^9$ together comprise a ring system as above defined include the indoles (XII)

(XII)

wherein $Z^{11}$ is alkyl of 1 to 4 carbon atoms. Conversion of the indoles to the compounds of formula (I) may be effected ozonolysis and subsequent treatment with dimethylsulphide or with zinc dust in acetic acid, or by chromic acid hydrolysis.

(8) A further method comprises conversion of a compound of formula (XIII)

(XIII)

wherein $Y^1$ and $Q^1$ are as defined in formula (I) and at least one of $Z^{12}$, $Z^{13}$ and $Z^{14}$ is an atom or group replaceable by or convertible to respectively $Y^2$, $Y^3$ or $Y^4$ as defined in formula (I) and the other(s), if any, of $Z^{12}$, $Z^{13}$ and $Z^{14}$ are respectively $Y^2$, $Y^3$ or $Y^4$.

Thus as one possibility a hydrogen atom may be replaced by an alkyl group by means of the Friedel-Crafts reaction using an alkylating agent (conveniently an appropriate alkyl halide, for example the chloride) and a catalyst such as aluminium chloride, stannic chloride or boron trifluoride. A t-butyl may also be introduced by reaction with t-butanol in the presence of an acid catalyst such as concentrated phosphoric acid.

A hydrogen atom may be replaced by a halogen by conventional techniques. Thus chlorination may be effected using for example t-butyl hypochlorite in acetic acid whilst iodination may be connected using for example either iodine monochloride or iodine and potassium iodide in solution in concentrated ammonia.

Suitable precursors for a hydroxyl group are groups —$OZ^2$ where $Z^2$ has the identities recited supra, the hydroxyl group being generality therefrom by procedures as previously described herein. Within this generality may particularly be mentioned the conversion, in the manner described, of alkoxy and benzyloxy groups to the hydroxyl group. Conversely a hydroxyl group may be converted to an alkoxy or benzyloxy group by reacting an appropriate compound (XIII), in a manner analogous to that described in respect of method (1) supra, with a compound $Z^1$–$Z^{15}$ wherein $Z^1$ is as previously defined and $Z^{15}$ is respectively alkyl or benzyl.

The compound of formula (I) wherein X is carboxyl or 5-tetrazolyl may be isolated as such or as salts thereof and it will be appreciated that the said compounds may be converted to salts thereof, and the reverse, and the salts converted to salts formed with other cations, by techniques well-known and conventional in the art. Thus, those salts which are not themselves pharmacologically acceptable are of value in the preparation of the parent carboxyl or 5-tetrazolyl compounds and of pharmacologically acceptable salts thereof. Similarly, addition salts of appropriate compounds of formula (I) with non-pharmacologically acceptable acids may be used in the preparation of the parent ethers and of pharmacologically acceptable acid addition salts thereof.

When the preparative procedures herein described provide a mixture of optical isomers of a compound of formula (I) or of an intermediate thereto, the individual isomers may be separated by appropriate conventional techniques.

The compound of formula (I), as above defined, may be used in medicine in the palliation of haemoglobinopathies and in particular for alleviating the symptoms of sickle-cell anaemia and mitigating the stufferings of those having the condition. The compounds may be used both on a regular maintenance basis and for the relief of acute crisis states.

The compounds may be administered to the human recipient by a route selected from oral, parenteral (including subcutaneous, intradermal, intramuscular and intravenous) and rectal. The size of an effective palliative dose of a compound will depend upon a number of factors including the identity of the recipient, the type of haemoglobinopathy involved, the severity of the condition to the treated and the route of administration and will ultimately be at the discretion of the attendant physician. In guiding him in assessing the efficacy and acceptability of a regimen the physician may have recourse not only to changes in the recipient's gross condition but also to in vitro haematological procedures standard in the art, for example those specifically mentioned herein and also the arythrocyte filterability test described in the Dean and Schechter reference supra and in U.S. Pat. No. 4,137,309.

Such an effective dose will generally be in the range 1 to 500 mg/kg bodyweight of human recipient per day, preferably in the range 5 to 100 mg/kg bodyweight per day and most preferably in the range 10 to 50 mg/kg bodyweight per day; an optimum dose is 20 mg/kg bodyweight per day. Unless otherwise indicated all weights are calculated as the carboxyl or 5-tetrazolyl acid of formula (I): for compounds within the said formula wherein X is other than carboxyl or 5-tetrazolyl the figures would be amended proportionately.

The desired dose is preferably presented as between two and four sub-doses administered at appropriate intervals throughout the day. Thus where three sub-doses are employed each will generally lie in the range 0.33 to 167, preferably 1.67 to 33.3 and most preferably 3.33 to 16.7 mg (acid)/kg bodyweight with an optimum of 6.67 mg (acid)/kg bodyweight. A daily dose for a human weighing of the order of 50 will thus generally lie in the range 50 mg. to 25 g (acid), preferably in the range 250 mg. to 5 g (acid) and most preferably in the range 500 mg to 2.5 g (acid) and may be conveniently presented as three equal unit sub-doses of 16.7 mg to 8.33 g (acid), preferably 83.3 mg to 1.67 g (acid) and most preferably 167 mg to 833 mg (acid). Optimally a human daily dose is 1.0 g (acid) conveniently presented as three unit sub-doses each of 333 mg (acid).

While it is possible for the compounds of formula (I) to be administered as the raw chemical it is preferable to present them as a pharmaceutical formulation preparation. The formulation of the present invention comprises a compound of formula (I), as above defined, together with one or more acceptable carriers therefore and optionally other therapeutic ingredients. The carrier(s) must be 'acceptable' in the sense of being compatible with the other ingredients of the formulation and not deleterious to the recipient thereof.

The formulation include those suitable for oral, parenteral (including subcutaneous, intradermal, intramuscular and intravenous) and rectal administration although the most suitable route may depend upon for example the condition of the recipient. The formulations may conveniently be presented in unit dosage form and may be prepared by any of the methods well known in the art of pharmacy. All methods include the step of bringing into association the compound of formula (I) (the active ingredient) with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid different. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipients; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter.

Preferred unit dosage formulations are those containing a daily dose or unit daily sub-dose, as hereinabove recited, or an appropriate fraction thereof, of a compound of formula (I).

It should be understood that in addition to the ingredients particularly mentioned above the formulations of this invention may include other agents conventional in the art having regard to the type of formulation in question, for example those suitable for oral administration may include flavouring agents.

The compounds of formula (I) may also be presented as depot formulations of the kind known in the art from which the active ingredient is released, over a prolonged period, once the formulation is in place within the body of the recipient.

A further application for the compounds, of formula (I) is the extracorporeal treatment of blood from the patient. As one possibility such treatment may be conducted in a batch-wise manner by removing an appropriate volume of blood, admixing it with the compound and transfusing the treated blood back into the patient. As an alternative possibility the treatment may be on a continuous basis, analogous to the well-known techniques for haemodialysis, whereby for a period of time blood is continuously withdrawn, admixed with the compound and passed back into the patient. Both procedures should be conducted under sterile conditions and may be repeated as often as necessary: in either case the treatment may be monitored by means inter alia of the in vitro procedures previously mentioned. An effective blood concentration of the compound of formula (I) will generally be in the range 0.1 mM to 100 mM, preferably in the range 0.3 mM to 33 mM and most preferably in the range 1 mM to 10 mM, with an optimum concentration of 3 mM.

The compounds of formula (I), as above defined, are also of value in the following further areas of human medicine.

(i) The palliation of pulmonary dysfunction, especially in emphysema or chronic bronchitis.

Pulmonary emphysema may be defined in pathological terms as an increase in the size of the air spaces distal to the terminal bronchioles, with destruction of their walls. In clinical practice the disease is associated also with chronic airflow obstruction.

Chronic bronchitis may be defined as chronic or recurrent cough with expectoration which cannot be attributed to conditions other than non-specific lung disease.

(ii) Protection from the effects of hypoxia, for example the hypoxia encountered at high altitude.

(iii) The radiosensitization of tumours (i.e. the tumours are made more sensitive to radiation), as an adjunct to tumour radiotherapy.

For each of these further utilities the compounds of formula (I), as above defined, may be administered to the human recipient by the same routes, at the same doses and sub-doses and as the same pharmaceutical formulations are hereinabove described in respect of their use in the palliation of haemoglobinopathies, although it will be appreciated that the size of an effective dose will again depend upon the same general considerations as indicated hereinbefore, namely, the identity of the recipient, the condition involved and its severity and the route of administration, and that the most suitable route may depend for example upon the condition of the recipient. Where it is clinically desirable the compounds may also be used, in the same manner as hereinabove set forth, in the extracorporeal treatment of the patient's blood.

The compounds formulae (II) to (XIII) as hereinbefore defined may be prepared by those methods known in the art for the synthesis of compounds of analogous structure: in particular, the compounds of formulae (IV), (V), (VI), (VII), (VIII), (IX), (X), (XI), (XII) and (XIII) as hereinbefore defined may be prepared inter alia by methods analogous to those taught herein in respect of the compounds of formula (I) using appropriate starting materials and conditions an hereinbefore described.

It will be understood from the foregoing description that this invention may comprise any novel feature described herein, principally but not exclusively for example:

(a) Compounds of formula (I) as hereinbefore defined and salts thereof.

(b) Methods as hereinbefore described for the preparation of compounds according to (a) supra, together with the compounds when so prepared.

(c) Compounds of formula (I) as hereinbefore defined and pharmacologically acceptable salts thereof, for use in the medical treatment of a human being.

(d) Compounds of formula (I) as hereinbefore defined and pharmacologically acceptable salts thereof, for use in the palliation in a human being of a haemoglobinopathy.

(e) Compounds of formula (I) as hereinbefore defined and pharmacologically acceptable salts thereof, for use in the palliation in a human being of sickle-cell anaemia.

(f) A pharmaceutical formulation comprising a treatment-effective amount of a compound of formula (I) as hereinbefore defined or a pharmacologically acceptable salt thereof together with an acceptable carrier therefor.

(g) A method for the preparation of a formulation according to (f) supra comprising admixture of the active ingredient, as defined, with the carrier therefor.

(h) A method for the palliation of a haemoglobinopathy comprising administering to a human being having such a condition a nontoxic, effective haemoglobinopathy palliative amount of a compound of formula (I) as hereinbefore defined or a pharmacologically acceptable salt thereof.

(i) A method according to (h) supra wherein the haemoglobinopathy is sickle-cell anaemia.

(j) Novel compounds of formula (II) to (XIII) as hereinbefore defined, methods for their preparation as hereinbefore described and the compounds when so prepared The following Examples are provided in illustration of the present invention and should not be construed as in any way constituting a limitation thereof. All temperatures are in degrees Celsius.

EXAMPLE 1

Preparation of 7-(2-formyl-3-hydroxyphenoxy)heptanoic acid (A) Ethyl 7-(2-formyl-3-methoxyphenoxy)heptanoate 2-Hydroxy-6-methoxybenzaldehyde (3.04 g, 0.02 M), ethyl 7-bromoheptanoate (4.74 g, 0.02 M), anhydrous potassium carbonate (2.97 g), sodium iodide (0.12 g) and ethanol (27 ml) were refluxed with stirring for 19 hr. The cooled reaction mixture was filtered and the solid washed with ethanol. The filtrate was evaporated to dryness and the residue partitioned between ether (40 ml) and water (40 ml). The organic layer was separated and washed with ZN sodium hydroxide solution, water, dried (sodium sulphate) and evaporated to give ethyl 7-(2-formyl-3-methoxyphenoxy)heptanoate, 4.2 g, 68% as an oil.

(B) 7-(2-Formyl-3-hydroxyphenoxyheptanoic acid

To a stirred solution of ethyl 7-(2-formyl-3-methoxyphenoxy)heptanoate (4.15 g, 0.0135 M) in dry tetrahydrofuran (60 ml) was added dropwise a solution of magnesium iodide (5.82 g, 0.0202 M) in dry ether (97.5 ml). The mixture was then stirred under reflux (5 hr). The cooled mixture was poured into 10% hydrochloric acid (65 ml). The organic layer was separated and the aqueous phase extracted with ethyl acetate. The combined organic solution were washed with water and evaporated to dryness. The residue, ethyl 7-(2-formyl-3-hydroxyphenoxyheptanoate, was dissolved in 2 N sodium hydroxide solution (50 ml) with stirring at room temperature (10 hr). The solution was decanted from a residue and acidified with concentrated hydrochloric acid with cooling. The precipitated solid was filtered off and washed well with water to give 7-(2-formyl-3-hydroxyphenoxy)heptanoic acid, m.p. 106°–107° C. from benzene/petrol.

EXAMPLE 2

Preparation of 5-(2-formyl-3-hydroxy-4-n-propoxyphenoxy)pentanoic acid (A) 3-Methoxy-4-n-propoxyacetophenone Acetovanillone (71.55 g, 0.43 M), anhydrous potassium carbonate (59.48 g), n-propyl iodide (96.72 g, 0.57 M) and acetone (1.5 L) were refluxed with stirring (16 hr). The cooled reaction mixture was evaporated to dryness and the residue treated with water. The solid product was filtered off, washed well with water and dissolved in ethyl acetate. After stirring with sodium sulphate and charcoal, the mixture was filtered and the filtrate evaporated to dryness. The solid residue was recrystallised from petrol (40–60) to give 3-methoxy-4-n-propoxyacetophenone, m.p. 40°–41° C.

(B) 5-Acetoxy-2-n-propoxyanisole

3-Methoxy-4-n-propoxyacetopehnone (47.25 g, 0.227 M), m-chloroperoxybenzoic acid (60 g) and 1.2-dichloroethane (500 ml) were stirred at room temperature in the absence of light (2.5 hr) and then allowed to stand overnight. A further 15 g of m-chloroperoxybenzoic acid was added and the mixture again stirred at room temperature in the absence of light (6 hr) and then stood over the weekend. The reaction mixture was diluted with ether and the resulting solution washed thoroughly with 2 N sodium hydroxide solution, water, dried (sodium sulphate) and evaporated to give 5-acetoxy-2-propoxyanisole.

(C) 3-Methoxy-4-n-propoxyphenol

5-Acetoxy-2-n-propoxyanisole (39.9 g, 0.178 M), 1.67 N sodium hydroxide solution (300 ml) and methanol (300 ml) were refluxed with stirring (1 hr). The methanol was then removed, the residue diluted with water and extracted with ether. The aqueous phase was acidified with concentrated hydrochloric acid and extracted with ether. The combined extracts were washed with water, dried (sodium sulphate) and evaporated. The product was then passed through a short pad of florisil eluting with chloroform-methanol (95:5) and the filtrate evaporated to give 3-methoxy-4-n-propoxyphenol as an oil which solidified on standing. After trituration with 40/60 petrol and filtration the product had m.p. 54°–56° C.

(D) 3-Methoxy-4-n-propoxyphenol tetrahydropyranyl ether

3-Methoxy-4-n-propoxyphenol (19.62 g, 0.108 M) was added in portions to a stirred mixture of dihydropyran (15.7 ml) and concentrated hydrochloric acid (3 drops) under nitrogen such that the temperature did not rise above 50° C. The solution was then stirred at room temperature (3 hr). The reaction mixture was diluted with ether and washed with water, 2 N sodium hydroxide solution, water, dried (sodium sulphate) and evaporated to give 3-methoxy-4-n-propoxyphenol tetrahydropyranyl ether.

(E) 6-Hydroxy-2-methoxy-3-n-propoxybenzaldehyde 1 ml of bromobenzene (11.88 ml) was added to a mixture of lithium chips (1.63 g) and anhydrous ether (90 ml) under nitrogen. When the reaction had commenced the remainder of the bromobenzene was added dropwise to the stirred mixture at such a rate as to cause gentle refluxing. After the addition was complete the mixture was stirred and refluxed (1 hr) and then cooled to room temperature. 3-Methoxy-4-n-propoxyphenol tetrahydropyranyl ether (30.03 g, 0.113 M) was added dropwise to the stirred mixture and then stirred at room temperature (3 days). A solution of anhydrous dimethyl formamide (8.5 ml) in anhydrous ether (8.5 ml) was added dropwise to the stirred mixture at such a rate as to cause gentle refluxing, and then stirred for an extra hour. The reaction mixture was poured into 2 N sulphuric acid/ice (200 ml) and extracted with ethyl acetate. The combined extracts were washed with water, dried (sodium sulphate) and evaporated. The residue was dissolved in 95% ethanol (175 ml) and 2 N hydrochloric acid (210 ml) was added. After stirring at room temperature (2 hr) the mixture was diluted with water (500 ml) and extracted with ethyl acetate/ether (1:1). The combined extracts were extracted with 2 N sodium hydroxide solution, the combined aqueous phases acidified with concentrated hydrochloric acid and extracted with ethyl acetate. The combined extracts were washed with water, dried (sodium sulphate) and evaporated. The residue was chromatographed on silica (MFC) eluting with chloroform-methanol (98:2) to give 6-hydroxy-2-methoxy-3-n-propoxybenzaldahyde as an oil.

(F) Ethyl 5-(2-formyl-3-methoxy-4-n-propoxyphenoxy)pentanoate

6-Hydroxy-2-methoxy-3-n-propoxybenzaldehyde (5.25 g, 0.025 M), ethyl 5-brown pentanoate (3.96 ml, 0.025 M), anhydrous potassium carbonate (3.71 g). sodium iodide (0.15 g) and 95% ethanol (50 ml) were refluxed with stirring for 16 hr. The cooled reaction mixture was filtered and the solid washed well with ethanol. The filtrate was evaporated to dryness and the residue partitioned between ether and water. The organic layer was separated and washed with 2 N sodium hydroxide solution, water, dried (sodium sulphate) and evaporated to give ethyl 5-(2-formyl-3-methoxy-4-n-propoxyphenoxy)pentanoate as an oil.

(G) 5-(2-Formyl-3-hydroxy-4-n-propoxyphenoxy)pentanoic acid 2.5 ml of a solution of iodine (6.64 g, 0.026 M) in anhydrous ether (80 ml) was added to a stirred mixture of magnesium metal (2.53 g, 0.105 g. atom) and ether (12.5 ml). When the reaction had commenced the remainder of the iodine solution was added dropwise at such a rate as to cause gentle refluxing. After the addition was complete the reaction mixture was heated to reflux until a colourless solution was obtained (15 mins). The cooled reaction mixture was filtered and the unreacted magnesium metal was washed with ether. The colourless solution of magnesium iodide thus obtained was added dropwise to a stirred solution of ethyl 5-(2-formyl-3-methoxy-4-n-propoxyphenoxy)pentanoate (5.95 g, 0.0176 M) in anhydrous tetrahydrofuran (50 ml). The mixture was brought to reflux with stirring for 5.5 hr. The cooled reaction mixture was poured into 2 N hydrochloric acid (75 ml). The organic layer was separated and the aqueous layer was extracted with ethyl acetate. The combined extracts were washed with water, dried (sodium sulphate) and evaporated. The residue was dissolved in 95% ethanol (50 ml). 2 N sodium hydroxide solution (50 ml) added and the mixture stirred at room temperature (4 hr). After evaporation of the ethanol the residue was diluted with water, washed with ether and acidified with concentrated hydrochloric acid. The oily product was extracted with ether, the combined extracts washed with water and extracted with 5% sodium bicarbonate solution. The combined extracts were acidified with concentrated hydrochloric acid to pH3 with ice cooling, and the gummy solid produced was filtered off and washed with water. This was chromatographed on kieselgel G (200 g) eluting with chloroform-methanol (9:1), the combined fractions evaporated and the residue recrystallised from benzene-petrol to give 5-(2-formyl-3-hydroxy-4-n-propoxyphenoxy)pentanoic acid, m.p. 78°–79° C. (Found: C, 60.65; H, 6.96, $C_{15}H_{20}O_6$ requires C, 60.80; H, 6.80%).

EXAMPLE 3

Preparation of 5-(4,6-dichloro-2-formyl-3-hydroxyphenoxy)pentanoic acid (A) Ethyl 5-(2-formyl-3-benzyloxyphenoxy)pentanoate A mixture of 2-hydroxy-6-benzyloxybenzaldehyde (3.0 g, 0.013 M), ethyl 5-bromopentanoate (2.75 g, 0.013 M), anhydrous potassium carbonate (2.16 g, 0.0156 M), sodium iodide (0.195 g) and dry dimethylformamide (15 ml) were stirred at 60°–80° C. for 3 hours and then left to stir at room temperature overnight. The mixture was then poured into water (50 ml) and the product extracted with ether (2×80 ml) and the combined extracts washed with 10% aqueous sodium hydroxide (2×20 ml) and then with water to neutrality, dried, and evaporated to give ethyl 5-(2-formyl-3-benzyloxyphenoxy)-pentanoate, (4.0 g, 86%) as a pale yellow oil.

(B) 5-(2-Formyl-3-benzyloxyphenoxy)pentanoic acid

A mixture of ethyl 5-(2-formyl-3-benzyloxyphenoxy)pentanoate (3.61 g, 0.01 M), potassium hydroxide (1.19 g, 0.021 M) and ethanol (40 ml) were stirred at 50°–60° C. for 5 hours. The ethanol was then removed in vacuo, the residue dissolved in water (50 ml) and the solution extracted with ether (2×80 ml). The aqueous layer was then acidified by the addition of 2N aqueous hydrochloric acid and the product extracted with ether (3×50 ml), and the combined extracts washed with water to neutrality, dried, and concentrated in vacuo to give 5-(2-formyl-3-benzyloxyphenoxy) pentanoic acid, 3.0 g, 91% as a yellow oil which crystallised on standing. The crude solid was crystallised from benzene/petroleum spirit 30°–40° C. to give pale cream crystals m.p. 110° C.

(C) 5-(2-Formyl-3-hydroxyphenoxy)pentanoic acid

A solution of 5-(2-formyl-3-benzyloxyphenoxy) pantanoic acid (1:0 g, 0.003 M) in ethanol containing 5% palladium on charcoal catalyst (0.61 g) was hydrogenated at atmospheric pressure. After 20 minutes the reaction was complete and the catalyst was filtered off and the ethanol removed in vacuo to give 5-(2-formyl-3-hydroxyphenoxy)pentanoic acid, m.p. 94° C.

(D) 5-(4,5-Dichloro-2-formyl-3-hydroxyphenoxy)pentanoic acid

To a well stirred suspension of 5-(2-formyl-3-hydroxyphenoxy)pentanoic acid (0.475 g, 0.002 M) in 90% acetic acid (1 ml) was added tert-butyl hypochlorite (0.5 ml) dropwise. The reaction mixture became warm and a clear solution resulted. This was stirred at room temperature (¾ hr) and then diluted with water. The oily product was extracted with ethyl acetate and the combined extracts washed with water, dried (sodium sulphate) and evaporated. The residue was chromatographed on kieselgel G (50 g) eluting with chloroform-methanol (95.5). The combined fractions were evaporated and the residue recrystallised from benzene-petrol to give 5-(4,6-dichloro-2-formyl-3-hydroxyphenoxy)pentanoic acid, m.p. 85°–87° C. (Found: C, 46.69; H, 3.92. $C_{12}H_{12}Cl_2O_5$ requires C. 46.92; H, 3.94%).

EXAMPLE 4

Preparation of 5-(2-formyl-3-hydroxyphenoxy)-N-methylsulphonyl-pentanamide (A) 5-(4-Benzofuranyloxy)pentanoic acid 4-Hydroxybenzofuran (4.9 g. 0.0366 M), ethyl 5-bromopentanoata (7.64 g, 0.0366 M), anhydrous potassium carbonate (5.44 g), sodium iodide (0.2 g) and 95% ethanol (20 ml) were refluxed with stirring for 4.5 hr. The cooled reaction mixture was filtered and the solid washed well with ethanol. The filtrate was evaporated to dryness and the residue partitioned between ether and water. The organic layer was separated and washed with 2N sodium hydroxide solution, water, dried (sodium sulphate) and evaporated to give ethyl 5-(4-benzofuranyloxy)pentanoata as an oil. To this oil was added 95% ethanol (130 ml) and 0.5N sodium hydroxide solution (130 ml) and the mixture stirred at room temperature (3 hr). The solution was evaporated to half-volume, diluted with water and extracted with ether. The aqueous phase was treated with charcoal, filtered and acidified with concentrated hydrochloric acid. The precipitated solid was filtered off, washed wall with water and recrystallised from ethanol-water to give 5-(4-benzofuranyloxy)pentanoic acid, m.p. 107.5°–108.5° C. (Found: C. 66.51; H, 5.90. $C_{13}H_{14}O_4$ requires C, 66.65; H, 6.02%).

(B)
5-(4-Benzofuranyloxy)-N-methylsulphonylpentanamide

To a stirred solution of 5-(4-benzofuranyloxy)pantanoic acid (1.485 g. 0.00635 M) in dry dimethyl formamide (25 ml) at 0° C. was added dry triethylamine (0.71 g. 0.00703 M), followed by iso-butylchloroformate (0.95 g, 0.00696 M), and this mixture was stirred at 0° C. for 25 mins.

Sodium metal (0.75 g. 0.0326 g atom) was dissolved in dry methanol (6.25 ml) and the resulting solution was added to a solution of methanesulphonamide (3.02 g. 0.318 M) in dry methanol (10 ml). The solution was evaporated under reduced pressure and the residual solid (sodium methanesulphonamide) treated with benzene and re-evaporated. The sodium methanesulphonamide, so prepared, was adeed to the solution of the mixed anhydride followed by HMPA (6.25 ml) and the mixture stirred at room temperature overnight. The reaction mixture was diluted with 2 N hydrochloric acid (60 ml) and extracted with ethyl acetate. The combined extracts were extracted with 5% sodium carbonate solution (2×65 ml). The combined extracts were acidified with concentrated hyrochloric acid and extracted with ethyl acetate. The combined organic phases were dried (sodium sulphate) and evaporated. The residue was recrystallised from benzenepetrol to give 5-(4-benzofuranyloxy)-N-methylsulphonylpentanamide, m.p. 110°–112° C. (Found: C. 53.91; H, 5.70; N, 4.58; S, 10.31. $C_{14}H_{17}NSO_5$ requires C, 54.00; H, 5.50; N, 4.50; S, 10.30).

(C)
5-(2-Formyl-3-hydroxyphenoxy)-N-methylsulphonylpentanamide 5-(4-Benzofuranyloxy)-N-methylsulphonylpentanamide (0.933 g, 0.003 M) was dissolved in dry methanol (135 ml) and cooled to −65° C. with stirring and exclusion of moisture. Ozonised air was bubbled through the solution at a rate of 20 liters/hr for 45 mins. Nitrogen was then bubbled through the solution (5 mins) to remove excess ozone before the addition of dimethyl sulphide (0.9 ml). The mixture was allowed to warm to room temperature overnight (16 hr). The solvent was removed in vacuo, the residue dissolved in ethyl acetate-ether (1:1), washed with water and extracted with 5% sodium bicarbonate solution. The combined extracts were acidified with concentrated hydrochloric acid the precipitated solid was filtered off, washed wall with water and recrystallised from ethyl acetate-petrol to give 5-(2-formyl-3-hydroxyphenoxy)-N-methylsulphonylpentanamide, m.p. 136°–138° C. (Found: C, 49.54; H, 5.33; N. 4.12, S, 10.14. $C_{13}H_{17}NSO_6$ requires C, 49.51; H, 5.43; N, 4.44; S, 10.17%).

EXAMPLE 5

Preparation of ethyl 4-(2-formyl-3-hydroxyphenoxymethyl)benzoate (A) Ethyl 4-(4-benzofuranyloxymethyl)benzoate 4-Hydroxybenzofuran (1.34 g, 0.01 M), ethyl 4-bromomethylbenzoate (2.43 g, 0.01 M), anhydrous potassium carbonate (1.49 g), sodium iodide (0.05 g) and 95% ethanol (10 ml) were refluxed with stirring (5 hr). The cooled reaction mixture was diluted with 0.5 N sodium hydroxide solution and cooled in ice. The precipitated solid was filtered off, washed well with water and recrystallised form ethanol-water to give ethyl 4-(4-benzofuranyloxymethyl)benzoate, m.p. 70°–72° C. (Found: C, 72.79; H, 5.46. $C_{18}H_{16}O_4$ requires C, 72.96; H, 5.44%).

(B) Ethyl 4-(2-formyl-3-hydroxyphenoxymethyl)benzoate

Ethyl 4-(4-benzofuranyloxymethyl)benzoate (1.84 g, 0.004 M) was dissolved in absolute ethanol (180 ml) and cooled to −65° C. with stirring and exclusion of moisture. Ozonised air was bubbled through the solution at a rate of 20 liters/hr for 1 hr. Nitrogen was then bubbled through the solution (5 mins) to remove excess ozone before the addition of dimethyl sulphide (1.2 ml). The mixture was allowed to warm to room temperature overnight (16 hr.). The solvent was removed in vacuo and the residue recrystallised from ethyl acetate-petrol to give ethyl 4-(2-formyl-3-hydroxyphenoxymethyl)-benzoate, m.p. 105°–107° C. (Found: C, 67.59; H, 5.21. $C_{17}H_{16}O_5$ requires C, 67.99; H, 5.37%).

EXAMPLE 6

Preparation of 4-(2-formyl-3-hydroxyphenoxymethyl)benzoic acid

Ethyl 4-(2-formyl-3-hydroxyphenoxymethyl)benzoate (0.6 g. 0.002 M) was suspended in 95% ethanol (5 ml) and 1 N sodium hydroxide solution (5 ml) and stirred at room temperature (2.5 hr). The yellow solution was diluted with water, extracted with ethyl acetate, and acidified with concentrated hydrochloric acid. The precipitated solid was filtered off, washed well with water, and recrystallised from 95% ethanol to give 4-(2-formyl-3-hydroxyphenoxymethyl) benzoic acid, m.p. 239°–240° C. (Found: C. 65.99; H, 4.29. $C_{15}H_{12}O_5$ requires C, 66.17; H, 4.44%).

EXAMPLE 7

Preparation of 5-(4-chloro-2-formyl-3-hydroxyphenoxy)pentanoic acid (A) 4-Chloro-3-methoxyphenol methoxymethyl ether 4-Chloro-3-methoxyphenol (4.755 g. 0.03 M), diemthoxymethane (10.26 g. 0.135 M), toluene-4-sulphonic acid (120 mg) and dry dichloromethane (180 ml) were refluxed under nitrogen and a soxhlet containing molecular sieve (type 3 A, previously dried at 120° C.) for 48 hr. After 24 hr a further 60 mg of toluene-4-sulphonic acid was added. On cooling, triethylamine (0.6 ml) was added and the solution washed with 1 N sodium hydroxide solution, water, dried (sodium sulphate) evaporated and the residue distilled in vacuo to give 4-chloro-3-methoxyphenol methoxymethyl ether, b.p. 83°–86° C./0.3 mmHg.

(B) 3-Chloro-6-hydroxy-2-methoxybenzaldehyde

4-Chloro-3-methoxyphenol methoxymethyl ether (3.1 g, 0.0153 M) in dry ether (3.5 ml) was added dropwise to a solution of phenyllithium (from 0.21 g lithium and 2.4 g bromobanzene) in dry ether (12 ml) under nitrogen and the mixture stirred at room temperature (3 days). A solution of dry dimethylformamide (1.12 g, 0.0153 M) in dry ether (1 ml) was then added dropwise over 15 mins and the mixture stirred at room temperature (1 hr). The reaction mixture was poured into 2 N sulphuric acid (100 ml) and extracted with ethyl acetate. The combined extracts were dried (sodium sulphate) and evaporated. The residue was dissolved in methanol (25 ml), 3 N hydrochloric acid (10 ml) added and the resultant solution stirred at 65° C. for 30 mins. The solvent was removed in vacuo and the residue diluted with water (50 ml) and extracted with ether. The combined extracts were dried (sodium sulphate) and evaporated. The residue was chromatographed on silica (MFC) eluting with chloroform. The fractions were combined and evaporated to give 3-chloro-6-hydroxy-2-methoxybenzaldehyde as an oil which crystallised on standing. (Found: m/e 186.0084. $C_8H_7ClO_3$ requires M185.0082).

(C) Ethyl 5-(4-chloro-2-formyl-3-methoxyphenoxy)pentanoate

3-Chloro-6-hydroxy-2-methoxybenzaldehyde (1.9 g, 0.0102 M), ethyl 5-bromopentanoate (2.13 g. 0.0102 M), anhydrous potassium carbonate (1.55 g), sodium iodide (56 mg), and 95% ethanol (25 ml) were refluxed with stirring (17 hr). The cooled reaction mixture was filtered and the solid washed well with ethanol. The filtrate was evaporated to dryness and the residue partitioned between ether and water. The organic layer was separated and washed with 2 N sodium hydroxide solution, water, dried (magnesium sulphate) and evaporated to give ethyl 5-(4-chloro-2-formyl-3-methoxyphenoxy)pentanoate as an oil.

(D) 5-(4-Chloro-2-formyl-3-hyroxyphenoxy)pantanoic acid

To a solution of ethyl 5-(4-chloro-2-formyl-3-methoxyphenoxy)pentanoate (2.0 g. 0.00636 M) in anhydrous tetrahydrofuran (30 ml) was added dropwise a solution of magnesium iodide (1.737 g. 0.00965 M) in anhydrous ether (50 ml). This mixture was then refluxed with stirring for 5 hr. The cooled reaction mixture was poured into 10% hydrochloric acid (30 ml). The organic layer was separated and the aqueous phase extracted with ethyl acetate. The combined organic phases were evaporated to dryness and the residue dissolved in 95% ethanol (50 ml). 2N sodium hydroxide solution (30 ml) added and the mixture stirred at room temperature (4 hr). The solution was evaporated to half volume, diluted with water and extracted with ethyl acetate. The aqueous phase was acidified with concentrated hydrochloric acid. The precipitated solid was filtered off, washed well with water and recrystallised from ethyl acetate-petrol to give 5-(4-chloro-2-formyl-3-hydroxphenoxy)pentanoic acid, m.p. 123°–124° C. (Found: C, 52.97; H, 4.69; Cl, 12.98. $C_{12}H_{13}ClO_5$ requires C, 52.84; H, 4.77; Cl, 13.03%).

EXAMPLE 8

Preparation of 5-(3-acetylamino-2-formylphenoxy)pentanoic acid

2-Acetylamino-6-hydroxybenzaldehyde (0.895 g, 0.005 M), ethyl 5-bromopentanoate (1.05 g. 0.005 M), anhydrous potassium carbonate (0.76 g), sodium iodide (50 mg) and 95% ethanol (20 ml) were refluxed with stirring for 16 hr. The cooled reaction mixture was filtered and the solid washed well with ethanol. The filtrate was evaporated to dryness and the residue partitioned between ether and water. The organic layer was separated and washed with 2 M sodium hydroxide solution, water, dried (sodium sulphate) and evaporated. The residue (ethyl 5-(3-acetylamino-2-formylphenoxy)pentanoate) was dissolved in 95% ethanol (20 ml) and treated with stirring over 1 hr with 1 N sodium hydroxide (4.5 ml), and then stirred at room temperature (2 hours). The solution was evaporated to one-third volume, diluted with water (10 ml) and acidified with concentrated hydrochloric acid with cooling. The precipitated solid was filtered off, washed well with water and recrystallised from benzene/petrol (charcoal) to give 5-(3-acetylamino-2-formylphenoxy)pentanoic acid, m.p. 119°–121° C. (Found: C, 60.55; H, 6.26; N, 4.88%. $C_{14}H_{17}NO_5$ requires C, 60.22; H, 6.09; N, 5.02%).

EXAMPLE 9

Preparation of 4-(2-formyl-3-hydroxyphenoxy)butanoic acid

(A) 4-(4-Benzofuranyloxy)butanoic acid

4-Hydroxybenzofuran (1.0 g., 0.00746 M), ethyl 4-bromobutanoate (1.46 g, 0.00746 M), anhydrous potassium carbonate (1.13 g), sodium iodide (50 mg) and 95% ethanol (20 ml) were reacted together to give ethyl 4-(4-benzofuranyloxy)butanoate which was subsequently hydrolysed, as previously described for the preparation of 5-(4-benzofuranyloxy)pentanoic acid, to give 4-(4-benzofuranyloxy)butanoic acid, m.p. 91°–93° C. (Found: C, 65.50; H, 5.40. $C_{12}H_{12}O_4$ requires C, 65.45; H, 5.45%).

(B) 4-(2-Formyl-3-hydroxyphenoxy)butanoic acid 4-(4-(Benzofuranyloxy)butanoic acid (0.66 g, 0.003 M) was dissolved in dry methanol (135 ml), cooled to −65° C. with stirring and ozonised as previously described for the preparation of 5-(2-formyl-3-hydroxyphenoxy)-N-methylsulphonylpentanamide, to give 4-(2-formyl-3-hydroxyphenoxy)butanoic acid, m.p. 151°–153° C. (Found: C, 58.70; H. 5.39. $C_{11}H_{12}O_5$ requires C. 58.93; H, 5.36%).

EXAMPLE 10

Preparation of 6-(2-formyl-3-hydroxyphenoxy)hexanoic acid

(A) 6-(4-Benzofuranyloxy)hexanoic acid

4-Hydroxybenzofuran (1.3 g, 0.0097 M), ethyl 6-bromohexanoate (2.17 g, 0.0097 M), anhydrous potassium carbonate (1.44 g), sodium iodide (60 mg) and 95% ethanol (10 ml) were reacted together to give ethyl 6-(4-benzofuranyloxy)-hexanoate which was subsequently hydrolysed, as previously described for the preparation of 5-(4-benzofuranyloxy)pentanoic awcid, to give 6-(4-benzofuranyloxy)hexanoic acid, m.p. 86°–87° C. (Found: C, 67.54; H. 6.48. $C_{14}H_{16}O_4$ requires C, 67.73; H. 6.50%).

(B) 6-(2-Formyl-3-hydroxyphenoxy)hexanoic acid p 5-(4-Benzofuranyloxy)hexanoic acid (0.495 g. 0.002 M) was dissolved in dry methanol (75 ml), cooled to −65° C. with stirring and ozonised as previously described for the preparation of 5-(2-formyl-3-hydroxyphenoxy)-N-methylsulphonylpentanamide, to give 6-(2-formyl-3-hyroxyphenoxy)hexanoic acid, m.p. 90°–92° C. (benzene-petrol). (Found: C, 61.88; H, 6.29. $C_{13}H_{16}O_5$ requires, C, 61,89; H, 6.39%).

EXAMPLE 11

Preparation of ethyl 4-(3-acetylamino-2-formylphenoxymethyl)benzoate

2-Acetylamino-6-hydroxybenzaldehyde (0.45 g, 0.0025 M), ethyl 4-bromomethylbenzoate (0.51 g, 0.0025 M), anhydrous potassium carbonate (0.38 g), sodium iodide (50 mg) and 95% ethanol (20 ml) were reacted together (4½ hr) to give ethyl 4-(3-acetylamino-2-formylphenoxymethyl)benzoate, m.p. 116°–119° C. (ethanol). (Found: C, 66.76; H, 5.61; N, 3.87%. $C_{19}H_{19}NO_5$ requires C, 66,85; H, 5.61; N, 4.10%).

EXAMPLE 12

Preparation of 4-(3-acetylamino-2-formylphenoxymethyl)benzoic acid

Ethyl 4-(3-acetylamino-2-formylphenoxymethyl)benzoate (0.45 g, 0.00132 N) was suspended in 95% ethanol (10 ml) with stirring and treated with 1N sodium hydroxide solution (1.32 ml) over 1 hour. The mixture was then diluted with water (3 ml) and stirred at room temperature overnight. A further 15 ml of water was added and the mixture stirred at room temperature (4 hr). The mixture was then extracted with ethyl acetate and the aqueous phase acidified with concentrated hydrochloric acid with cooling. The precipitated solid was filtered off, washed well with water, and recrystallised from ethanol to give 4-(3-acetylamino-2-formylphenoxymethyl)benzoic acid, m.p. 242°–244° C. (dec.) (Found: C, 65.27; H, 4.93; M, 4.23%. $C_{17}H_{15}NO_5$ requires C, 65.17; H, 4.83; N, 4.47%).

EXAMPLE 13

2-(2-Formyl-3-hydroxyphenoxymethyl)benzoic acid (A) Methyl 2-(2-methyl-4-benzofuranyloxymethyl)benzoate 4-Hydroxy-2-methylbenzofuran (2/3 g, 14.4 M), methyl 2-bromomethylbenzoate (3.29 g, 14.4 mM), anhydrous potassium carbonate (2.135 g), sodium iodide (87 mg) and methanol (20 ml) were reacted together in an analogous manner to that described in Example 5(A) to give methyl 2-(2-methyl-4-benzofuranyloxymethyl)benzoate, m.p. 93°–95° C. (Found: C, 72.74; H, 5.26. $C_{18}H_{16}O_4$ required C, 72.96; H, 5.44%).

(B) 2-(2-Formyl-3-hydroxyphenoxymethyl)benzoic acid

A mixture of methyl and ethyl 2-(2-methyl-4-benzofuranyloxymethyl) benzoates (1.212 g) was dissolved in absolute ethanol (180 ml) and ozonised in an analogous manner so that described in Example 5(B) to give a mixture of methyl and ethyl esters of 2-(3-acetoxy-2-formylphenoxymethyl)benzoic acid, as an oil. This oil was dissolved in 95% ethanol (15 ml) and treated with 1N sodium hydroxide solution (15 ml) in an analogous manner to that described in Example 6 to give 2-(2-formyl-3-hydroxyphenoxymethyl)benzoic acid, m.p. 218°–219.5° C. (Found: C, 65.91; H, 4.50. $C_{15}H_{12}O_5$ required C, 66.17; H, 4.44%).

EXAMPLE 14

5-[4-(2-formyl-3-hydroxyphenoxymethyl)phenyl]tetrazole (A) 4-(2-Methyl-4-benzofuranyloxymethyl)benzonitrile 4-Hydroxy-2-methylbenzofuran (5.18 g, 0.035 M), 4-bromomethylbenzonitrile (6.86 g, 0.035 M), anhydrous potassium carbonate (5.2 g), sodium iodide (0.21 g) and 95% ethanol (50 ml) were reacted together in an analogous manner to that described in Example 5(A) to give 4-(2-methyl-4-benzofuranyloxymethyl)benzonitrile, m.p. 84°–85° C. (Found: C, 77.57; H, 5.02; N, 5.22. $C_{17}H_{13}NO_2$ requires C, 77.55; H, 4.98; N, 5.32%).

(B) 5-[4-(2-methyl-4-benzofuranyloxymethyl)phenyl]tetrazole 4-(2-Methyl-4-benzofuranyloxymethyl)benzonitrile (3.92 g, 0.015 M), sodium oxide (0.97 g), ammonium chloride (0.8 g) and dimethylformamide (20 ml) were stirred and heated at 125°–130° C. for 3 hours. The mixture was cooled slightly and poured into a mixture of 2N sodium hydroxide, ice, and sodium nitrite (0.065 g). This mixture was extracted with ether and the aqueous phase acidified with conc. hydrochloric acid. The resulting solid was filtered off, washed with water, dried, and recrystallised from ethyl acetate/petrol to give 5-[4-(2-methyl-4-benzofuranyloxymethyl)phenyl]tetrazole, m.p. 196°–197° C. (Found: C, 66.79; H, 4.53; N, 18.28. $C_{17}H_{14}N_4O_2$ requires C, 66.65; H, 4.61; N, 18.29%).

(C) 5-[4-(2-Formyl-3-hydroxyphenoxymethyl)phenyl]tetrazole

5-[4-(2-Methyl-4-benzofuranyloxymethyl)phenyl]tetrazole (1.224 g, 0.004 M) was dissolved in a mixture of dry methanol (130 ml) and dry dimethylformamide (20 ml), and cooled to −65° C. with stirring and exclusion of moisture. Ozonised air was bubbled through the solution at a rate of 20 liters/hr for 1 hr. Nitrogen was then bubbled through the solution (5 mins). to remove excess ozone before the addition of dimethyl sulphide (1.2 ml). The mixture was allowed to warm to room temperature overnight (16 hr). The solvent was removed in vacuo and the residual oil dissolved in ethyl acetate and washed with 2 N hydrochloric acid, water, and extracted with sodium bicarbonate solution. The combined extracts were acidified with 2 N hydrochloric acid to give a solid which was filtered off and dried. This mixture of 5-[4-(2-formyl-3-hydroxyphenoxymethyl)phenyl]tetrazole and 5-[4-(3-acetoxy-2-formylphenoxymethyl)phenyl]tetrazole was suspended in 95% ethanol (20 ml) and 1N sodium hydroxide (20 ml) and stirred at room temperature (1 hr). The solution was evaporated and the residue diluted with water and acidified. The resulting solid was filtered off, washed with water, dried and recrystallised form ethanol/water to give 5-[4-(2-formyl-3-hydroxyphenoxymethyl)phenyl]tetrazole as the 0.5 hydrate, m.p. 206°–206.5° C. (Found: C, 59.00; H, 4.29; N, 18.46. $C_{15}H_{12}N_4O_3.0.5H_2O$ requires C, 59.01; H, 4.29; N, 18.35%).

EXAMPLE 15

5-(2-Formyl-3-hydroxy-4-methoxyphenoxy)pentanoic acid (A) 3,4-Dimethoxyphenol tetrahydropyranyl ether 3,4-Dimethoxyphenol (30.8 g) was added in small portions to a mixture of dihydropyran (29.2 ml) and conc. hydrochloric acid (3 drops) under nitrogen so that the temperature did not rise above 50° C. After the addition was complete the dark solution was stirred at room temperature for 3 hrs. and then diluted with ether. The resulting solution was washed with water, 2 N sodium hydroxide solution, water, dried (sodium sulphate) and evaporated to give 3,4-dimethoxyphenol tetrahydropyranyl ether.

(B) 2,3-Dimethoxy-6-hydroxybenzaldehyde 3,4-Dimethoxyphenol tetrahydropyranyl ether (47.6 g, 0.2 M) was lithiated with phenyllithium (from 21.02 ml bromobenzene and 2.89 g lithium), formylated by the addition of dry dimethylformamide (15 ml) and subsequently hydrolysed in an analogous manner to that described in example 2(E). The crude product was distilled under high vacuum to give 2,3-dimethoxy-6-hydroxybenzaldehyde as a yellow oil which solidified on standing. After trituration with 40/60 petrol and filtration the product had m.p. 53°–54° C. (Found: C, 59.18; H, 5.54. $C_9H_{10}O_4$ requires C, 59.33; H, 5.53%).

(C) 5-(2-Formyl-3-hydroxy-4-methoxyphenoxy)pentanoic acid 2,3-Dimethoxy-6-hydroxybenzaldehyde (5.46 g, 0.03 M), ethyl 5-bromopentanoate (6.273 g, 0.03 M), anhydrous potassium carbonate (4.45 g), sodium iodide (0.185 g) and 95% ethanol (25 ml) were reacted together in an analogous manner to that described in example 2(F) to give ethyl 5-(2-formyl-3,4-dimethoxyphenoxy)pentanoate as an oil. This ester was demethylated with magnesium iodide (from 7.18 g iodine) in an analogous manner to that described in example 2(C), except that the ethyl acetate solution obtained on work-up of the demethylation was extracted with 2 N sodium hydroxide solution. The combined extracts were acidified with conc. hydrochloric acid and the oily product extracted into ether. The combined extracts were washed with water, extracted with sodium bicarbonate solution and the combined extracts acidified to give a solid which was filtered off, washed with water and dried. The product was passed through a column of kieselgel eluting with chloroform-methanol (95:5) and the purified product was recrystallsedfrom benzene, m.p. 105°–107° C. (Found: C, 58.43; H, 3.96. $C_{13}H_{16}O_2$ requires C, 58.20; H, 6.01%).

EXAMPLE 16

3-(2-Formyl-3-hydroxyphenoxy)propionitrile (A) 3-(4-Benzofuranyloxy)propionitrile 4-Hydroxybenzofuran (2.68 g, 0.12 M), acrylonitrile (5.4 ml), and Triton B (0.2 ml) were refluxed on a steambath for 48 hrs. The cooled mixture was diluted with ether/ethyl acetate (1:3) (100 ml) and the solution washed with 1.5 N sodium hydroxide solution, 1N hydrochloric acid, water, dried (sodium sulphate) and evaporated to give 3-(4-benzoforanyloxy) propionitrile as a colourless oil which solidified in the refrigerator. (Found: M ⊕ 187,0633. $C_{11}H_9NO_2$ requires 187.0633).

(B) 3-(2-Formyl-3-hydroxyphenoxy)propionitrile 3-(4-Benzofuranyloxy)propionitrile (0.935 g, 8 μM) was dissolved in absolute ethanol (225 ml) and ozonised in an analogous manner to that described in example 5(B) to give 3-(2-formyl-3-hydroxyphenoxy)propionitrile which was recrystallised from ethyl acetate/petrol, m.p. 84°–86° C. (Found: C, 62.56; H, 4.79; N, 6.99. $C_{10}H_9NO_3$ requires C, 62.38; H, 4.71; N, 7.33%).

EXAMPLE 17

4-(2-Formyl-3-hydroxyphenoxymethyl)benzoic acid (A) Ethyl 4-(2-methyl-4-benzofuranyloxymethyl)benzoate 4-Hydroxy-2-methylbenzofuran (7.4 g, 0.05 M), ethyl 4-bromomethylbenzoate (12.15 g, 0.05 M), anhydrous potassium carbonate (7.59 g), sodium iodide (0.3 g), and 95% ethanol were reacted together in an analogous manner to that described in example 5(A) to give ethyl 4-(2-methyl-4-benzofuranyloxymethyl)benzoate which was recrystallised from ethanol/water, m.p. 59°–61° C. (Found: C, 73.73; H, 6.03. $C_{19}H_{18}O_4$ requires C, 73.55; H, 5.81%).

(B) Ethyl 4-(2-formyl-3-hydroxyphenoxymethyl)benzoate

To a stirred solution of the product of step (A) (10 g) in glacial acetic acid (200 ml) at 60°–70° C. was added a solution of sodium dichromate dihydrate (22.5 g) in water (50 ml), over 10 minutes. The reaction mixture was maintained at 70° C. for 1 hour and then diluted with water (1 L). The cloudy suspension was extracted with ethyl acetate (3×300 ml) and the combined extracts washed with water (3×200 ml) and brine (300 ml). After drying (magnesium sulphate) the solution was filtered through florisil (1 cm pnd) and evaporated to yield a red solid (9.8 g). This was dissolved in chloroform and passed down a florisil column (50 g, ~15 cm long) eluting with chloroform. The yellow fraction was collected and evaporated to give a yellow solid.

(C) 4-(2-Formyl-3-hydroxyphenoxymethyl)benzoic acid

The product from step (B) (7.9 g) was suspended in methanol (90 ml) and stirred with 1 N sodium hydroxide solution (90 ml) for 2.5 hours. The resulting dark solution was evaporated to half volume and then diluted with water (160 ml) and acidified with concentrated hydrochloric acid, with cooling in an ice bath. The precipitated product was collected by filtration, washed with water (200 ml), sucked dry and recrystallised from aqueous dimethylformamide. The title compound was isolated as yellow crystals after drying in vacuo at 60° C. m.p. 240°–242° C. ( sinters at ~225° C.)

EXAMPLE 18

4-(2-Formyl-3-hydroxyphenoxymethyl)benzoic acid (A) 4-Methoxymethoxy-2-methylbenzofuran To a stirred mixture of 4-hydroxy-2-methylbenzofuran (7.1 g, 0.048 M), anhydrous powdered potassium carbonate (19.87 g) and acetone (82 ml), was added dropwise bromomethoxymethane (11.99 g, 7.88 ml, 0.0959 M) with ice cooling. After the addition was complete the reaction mixture was stirred at room temperature overnight, filtered and evaporated. The residual oil was distilled to give 4-methoxymethoxy-2-methylbenzofuran, b.p. 94°–97° C./0.8 mmHg.

(B) 2-Hydroxy-6-methoxymethoxybenzaldehyde

4-Methoxymethoxy-2-methylbenzofuran (6.7 g, 0.0349 M) was dissolved in dry methanol (800 ml) and ozonised in an analogous manner to that described in example 5(B). After evaporation of solvent the residual oil (2-acetoxy-6-methoxymethoxybenzaldehyde dimethyl acetal) was dissolved in methanol (100 ml) and treated with 1 N sodium hydroxide solution (72 ml) with stirring at room temperature (2 hrs). The solution was evaporated to one-third volume, the residue diluted with water (100 ml) and acidified to pH 5 with citric acid. The liberated oil was extracted into ether, and the combined extracts evaporated. The residual oil (2-hydroxy-6-methoxymethoxybenzaldehyde dimethyl acetal) was dissolved in tetrahydrofuran (80 ml) and the solution treated with 5% citric acid solution (80 ml) with stirring at room temperature (2 hrs). The solution was evaporated to half-volume and diluted with water (80 ml). The mixture was extracted with ether and the combined extracts extracted with 1 N sodium hydroxide solution. The combined extracts were immediately acidified to pH 5 with solid citric acid, and the liberated oil extracted into ether. The combined extracts were washed with 5% sodium bicarbonate solution, water, dried (sodium sulphate) and evaporated to give 2-hydroxy-6-methoxymethoxybenzaldehyde as an oil which solidified on standing, m.p. 47°–49° C.

(C) Ethyl 4-(2-formyl-3-hydroxyphenoxymethyl)benzoate

To a stirred solution of 2-hydroxy-6-methoxymethoxybenzaldehyde (0.91 g, 5.1 mM) in dry dimethyl sulphoxide (8 ml) was added potassium t-butoxide (0.57 g, 5.1 mM) with exclusion of moisture. After 10 mins, ethyl 4-bromomethylbenzoate (1.22 g, 5 mM) was added and the whole stirred at room temperature (18 hrs). The reaction mixture was poured into water (100 ml) and the liberated oil extracted into ether. The combined extracts were washed with 5% sodium carbonate solution, water, dried (sodium sulphate) and evaporated. The residual oil (ethyl 4-(2-formyl-3-methoxymethoxyphenoxymethyl)benzoate was dissolved in ethanol (30 ml) and treated with 3 M hydrochloric acid (30 ml) with stirring at 60° C. (30 mins). The solid was filtered off, washed with water, dried, and recrystallised from ethanol/water to give ethyl 4-(2-formyl-3-hydroxyphenoxymethyl)benzoate, m.p. 105°–ω° C. (identical to a sample previously prepared, Example 5(B)).

(D) 4-(2-Formyl-3-hydroxyphenoxymethyl)benzoic acid

Ethyl 4-(2-formyl-3-hydroxyphenoxymethyl)benzoate was hydrolysed as previously described (Example 6) to give 4-(2formyl-3-hydroxyphenoxymethyl)benzoic acid, m.p. 239°–240° C.

EXAMPLE 19

Anti-sickling potency in vitro

In an aerated sample of whole homozygous human sickle cell blood, i.e. one maintained at an oxygen tension of 150 mm. Hg, the proportion of normal discoid erythrocytes is usually greater than 90%. If the oxygen tension is reduced the proportion of normal cells decreases because there is an inverse increase in the proportion of sickle and bizarre cells and at an oxygen tension of 28 mm. Hg the proportion of normal cells lies in the range 45–65%. In the presence of an effective concentration of an anti-sickling agent the proportion of normal cells at such low oxygen tensions is increased.

A suitable index of the in vitro anti-sickling potency (ASP) of a compound in whole homozygous human sickle cell blood may be calculated from the equation $$ASP = 100 \times \frac{(\% \text{ in test}) - (\% \text{ in control})}{(\% \text{ in aerated}) - (\% \text{ in control})}$$

wherein
"control" refers to blood samples maintained under a reduced oxygen tension (28 mm. Hg);
"test" refers to blood samples maintained at 28 mm. Hg as for "control" samples but containing a known concentration of test compound;
"aerated" refers to blood samples maintained at high oxygen tension (150 mm. Hg); and
the percentages refer to the proportion of normal discoid erythrocytes.

The potencies for a number of compounds are presented in the following table. A figure of less than 20 indicates that the compound is essentially inactive (at the test concentration) in this procedure while a negative number denotes an increase in sickling in the presence of the compound.

| Compound | Anti-sickling potency | | |
|---|---|---|---|
| | 2.0 mM | 3.0 mM | 10.0 mM |
| Ex. 1 | 59.5 | | |
| Ex. 2 | 73.5 | | |
| Ex. 3 | 27 | | |
| Ex. 4 | 55.5 | | |
| Ex. 6 | 71.5 | | |
| Ex. 7 | 62.5 | | |
| Ex. 8 | 33.5 | | |
| Ex. 9 | 63.5 | | |
| Ex. 10 | 72.5 | | |
| Ex. 13 | 65.5 | | |
| Ex. 14 | 45 | | |
| (A)* | | | 52 |
| (B)* | | −26 | |
| (C)* | | −7 | |

*These compounds have been taught in the literature as of value in the palliation of sickle-cell anemia, as follows:
(A): Potassium cyanite (see inter alia the Dean and Schachter reference supra)
(B): 3,4-Dihydro-2,2-dimethyl-2H-1 benzopyran-6-butyric acid Hatnre, 258, December 25, 1973, 743-746)
(C): Methylenebisphosphoric acid (U.S. Pat. No. 4 137 309)

EXAMPLE 20

Effect on the oxygen-dissociation curve of whole normal human blood in vitro

The compounds under investigation were separately added to aliquots of heparinised normal (AA genotype) adult human whole blood. Each sample was incubated (30 mins., 37° C.) and the oxygen-dissociation curve then determined using a whole-blood spectrophotometer (Hen-O-Scan, Trade Name).

Figure 1:
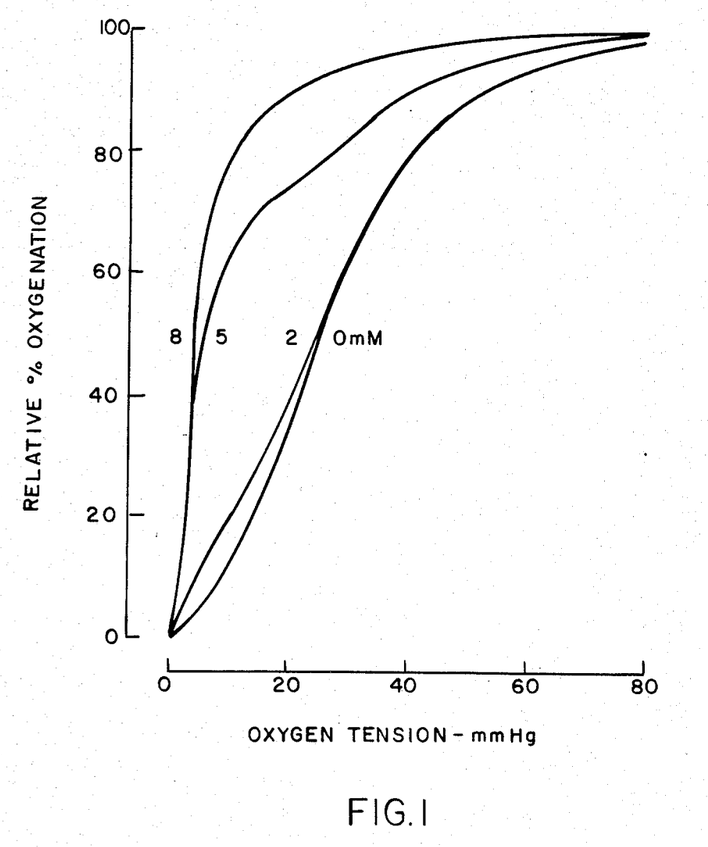

FIG. 1 shows the concentration-dependent left displacement of the dissociation curve seen with 4-(2-formyl-3-hydroxyphenoxymethyl) benzoic acid, the indicated concentrations being with respect to the whole-blood volume.

EXAMPLE 21

Toxicity Data

The acute oral $LD_{50}$ in mice of 4-(2-formyl-3-hydroxyphenoxymethyl) benzoic acid, administered as a solution in sodium bicarbonate-saline, was found to be approximately 400 mg/kg.

The acute $LD_{50}$ in rats of 4-(2-formyl-3-hydroxyphenoxymethyl) benzoic acid, administered as a solution in sodium bicarbonate-saline, was found to be in excess of 1 g./kg.

EXAMPLE 22

Pharmaceutical Formulations

| (A) TABLET | |
|---|---|
| Compound | 300 mg. |
| Lactose | 100 mg. |
| Starch | 50 mg. |
| Polyvinylpyrrolidone | 5 mg. |
| Magnesium Stearate | 5 mg. |
| | 460 mg. |

The compound, Lactose and Starch are mixed together and then granulated with a solution of Polyvinylpyrrolidone in water. After drying the granules, the Magnesium Stearate is mixed in and tablets compressed at an average weight of 460 mg.

| (B) CAPSULE | |
|---|---|
| Compound | 300 mg. |
| Dibasic Calcium Phosphate, Dihydrate | 100 mg. |
| Sodium Starch Glycolate | 16 mg. |
| Methylcellulose 400 cps | 5 mg. |
| Stearic Acid | 4 mg. |
| Talc | 5 mg. |
| | 430 mg. |

The compound, Dibasic Calcium Phosphate, Dihydrate and Sodium Starch Glycolate are mixed together and then granulated with a solution of the Methylcellulose in water. After drying, the granules are mixed with the Stearic Acid and Talc and the mixture filled into gelatin capsules at an average fill weight of 450 mg.

| (C) SUPPOSITORY | |
|---|---|
| Compound | 300 mg. |
| Suppository Base (Mixed Glycerides of saturated fatty acids) | 1700 mg. |
| | 2000 mg. |

Grind the Compound to a particle size below 150μ. Add the suppository base at 38°–40° C. Mix to give a uniform dispersion. Pour into suppository moulds and allow to cool.

| (D) INJECTION - Single dose, intravenous | |
|---|---|
| Compound | 300 mg. |
| Sodium Hydroxide Solution (301) | q.s. |

Water for injections to 5 ml. Suspend the compound in some of the water for injections. Adjust the pH to 10 to 10.5 by addition of sodium hydroxide solution. Add sufficient water for injections to produce the required final volume. Re-check the pH. Sterilise by passage through a sterile membrane filter of 0.22μ pore size. Fill under aseptic conditions into sterile vials and freeze dry.

| (E) INJECTION - Multidose, intramuscular | |
|---|---|
| Compound, sterile | 3000 mg. |
| Polysorbate 20 | 3 mg. |
| Polyvinylpyrrolidone | 1000 mg. |
| Chlorocresol | 60 mg. |
| Sodium Chloride | q.s. to isotonicity |
| Water for Injections to | 30 ml. |

Dissolve the Polysorbate 20, polyvinylpyrrolidone, sodium chloride and chlorocrosol in water for injections. Sterille filter, 0.22μ. Grind the sterile compound to a particle size below 20μ and add to the filtered solution. Mix until a uniform dispersion is achieved. Fill into sterile glass vials.

| (F) PROLONGED RELEASE TABLET | |
|---|---|
| Compound | 600 mg. |
| Casein | 195 mg. |
| Hydrogenated Castor Oil | 400 mg. |
| Magnesium Stearate | 5 mg. |
| | 1200 mg. |

Melt the Hydrogenated Castor Oil and add the compound, ground to a particle size of less than 150μ. Add the Casein. Mix until uniform. Allow to cool and mill to a granule. Mix in the Magnesium Stearate and compress to an average weight of 1,200 mg.

In the foregoing the "Compound" refers to a compound of formula (I) as hereinbefore defined, the weight thereof being calculated as the appropriate carboxyl or 5-tetrazolyl acid as hereinbefore described.

What we claim is:

1. 4-(2-Formyl-3-hydroxyphenoxymethyl)benzoic acid and salts thereof.

2. 4-(2-Formyl-3-hydroxyphenoxymethyl)benzoic acid.

3. A salt of the acid compound according to claim 2.

4. A pharmacologically acceptable salt of 4-(2-formyl-3-hydroxyphenoxymethyl)benzoic acid.

5. A pharmaceutical formulation comprising 4-(2-formyl-3-hydroxyphenoxymethyl)benzoic acid, or a pharmacologically acceptable salt thereof, together with an acceptable carrier therefor.

6. A formulation according to claim 5 in unit dosage form containing a non-toxic amount of the acid compound or salt.

7. A formulation according to claim 6 in the form of a tablet suitable for oral administration.

8. A formulation according to claim 6 in the form of a capsule suitable for oral administration.

9. A formulation according to claim 6 in the form of a sterile injection solution suitable for parenteral administration.

10. A method for the palliation of a haemoglobinopathy in a human being having such a condition which comprises administering to said human being a non-toxic, effective palliative amount of the acid according to claim 2 or a pharmacologically acceptable salt thereof.

11. A method as in claim 10 wherein the haemoglobinopathy is sickle-cell anaemia.

12. A method for the palliation of pulmonary dysfunction in a human being having such a condition which comprises administering to said human being a non-toxic, effective palliative amount of the acid according to claim 12 or a pharmacologically acceptable salt thereof.

13. A method as in claim 12 for the palliation of pulmonary emphysema.

14. A method as in claim 12 for the palliation of chronic bronchitis.

15. A method for protecting a human being requiring such treatment from the hypoxic effects of high altitude which comprises administering to said human being a non-toxic, effective protective amount of the acid according to claim 2 or a pharmacologically acceptable salt thereof.

16. A method for the radiosensitization of a tumor in a human being which comprises administering to a human being having a tumour a non-toxic, effective radiosensitizing amount of the acid according to claim 2 or a pharmacologically acceptable salt thereof.

17. The formulation according to claim 5 in a form for oral administration.

18. The formulation according to claim 5 in a form for parenteral administration.

19. The formulation according to claim 5 in a form for rectal administration.

20. A unit dosage formulation according to claim 6 containing 500 mg to 2.5 g (calculated as the acid) of the acid or salt.

21. A unit dosage formulation according to claim 6 containing 167 mg to 833 mg (calculated as acid) of the acid or salt.

* * * * *